United States Patent
Saptari

(10) Patent No.: US 9,651,422 B2
(45) Date of Patent: May 16, 2017

(54) MULTIPLEX TUNABLE FILTER SPECTROMETER

(71) Applicant: MKS Instruments, Inc., Andover, MA (US)

(72) Inventor: Vidi A. Saptari, Cambridge, MA (US)

(73) Assignee: MKS Instruments, Inc., Andover, MA (US)

( * ) Notice: Subject to any disclaimer, the term of this patent is extended or adjusted under 35 U.S.C. 154(b) by 0 days.

(21) Appl. No.: 14/518,974

(22) Filed: Oct. 20, 2014

(65) Prior Publication Data

US 2015/0103354 A1    Apr. 16, 2015

Related U.S. Application Data

(63) Continuation of application No. 12/755,980, filed on Apr. 7, 2010, now Pat. No. 8,896,839.

(Continued)

(51) Int. Cl.

| | |
|---|---|
| *G01J 3/45* | (2006.01) |
| *G01J 3/06* | (2006.01) |
| *G01J 3/32* | (2006.01) |
| *G01N 21/25* | (2006.01) |
| *G01N 21/31* | (2006.01) |

(Continued)

(52) U.S. Cl.
CPC . *G01J 3/06* (2013.01); *G01J 3/32* (2013.01); *G01N 21/255* (2013.01); *G01N 21/314* (2013.01); *G01J 2003/1247* (2013.01); *G01N 21/33* (2013.01); *G01N 21/3504* (2013.01); *G01N 2021/3174* (2013.01); *G01N 2201/129* (2013.01)

(58) Field of Classification Search
CPC .... G01N 21/255; G01N 21/314; G01N 21/33; G01N 21/3504; G01N 2021/3174; G01N 2021/129; G01J 2003/1247; G01J 3/06; G01J 3/32
USPC ....................................................... 356/455
See application file for complete search history.

(56) References Cited

U.S. PATENT DOCUMENTS

| | | |
|---|---|---|
| 2,834,246 A | 5/1958 | Foskett |
| 3,864,037 A | 2/1975 | Johnson |

(Continued)

OTHER PUBLICATIONS

PCT/US09/041254-A1, Feb. 12, 2009, Jin et al.
(Continued)

*Primary Examiner* — Tarifur Chowdhury
*Assistant Examiner* — Jonathon Cook
(74) *Attorney, Agent, or Firm* — Choate, Hall & Stewart LLP; William R. Haulbrook; Margo R. Monroe

(57) ABSTRACT

The invention provides spectroscopic systems and spectrometers employing an optical interference filter module having a plurality of bandpass regions. In certain embodiments, the systems include a mechanism for wavelength tuning/scanning and wavelength band decoding based on an angular motion of one or more filters. A spectral processing algorithm separates the multiplexed wavelength-scanned bandpass regions and quantifies the concentrations of the analyzed chemical and/or biological species. The spectroscopic system allows for compact, multi-compound analysis, employing a single-element detector for maximum performance-to-cost ratio. The spectroscopic system also allows for high-sensitivity measurement and robust interference compensation.

17 Claims, 13 Drawing Sheets

Related U.S. Application Data

(60) Provisional application No. 61/212,165, filed on Apr. 8, 2009.

(51) Int. Cl.
  *G01J 3/12* (2006.01)
  *G01N 21/33* (2006.01)
  *G01N 21/3504* (2014.01)

(56) References Cited

U.S. PATENT DOCUMENTS

| | | |
|---|---|---|
| 3,904,880 A | 9/1975 | Benz et al. |
| 4,040,747 A | 8/1977 | Webster |
| 4,563,090 A | 1/1986 | Witte |
| 4,759,625 A | 7/1988 | Caponi et al. |
| 4,770,478 A | 9/1988 | Cross et al. |
| 4,988,196 A | 1/1991 | Gilligan |
| 5,166,755 A | 11/1992 | Gat |
| 5,218,473 A | 6/1993 | Seddon et al. |
| 5,268,745 A | 12/1993 | Goody |
| 5,581,356 A | 12/1996 | Vezard |
| 5,663,894 A | 9/1997 | Seth et al. |
| 6,057,925 A | 5/2000 | Anthon |
| 6,229,402 B1 | 5/2001 | Kataoka et al. |
| 6,496,309 B1 | 12/2002 | Bliton et al. |
| 7,099,003 B2 | 8/2006 | Saptari et al. |
| 7,436,515 B2 | 10/2008 | Kaye et al. |
| 8,184,293 B2 | 5/2012 | Bonyuet et al. |
| 8,502,981 B2 | 8/2013 | Bonyuet et al. |
| 2003/0072680 A1 | 4/2003 | Higuchi et al. |
| 2003/0227628 A1* | 12/2003 | Kreimer .............. G01J 3/02 356/419 |
| 2006/0018514 A1 | 1/2006 | Bankhead |
| 2006/0250606 A1 | 11/2006 | Kaye et al. |
| 2006/0268266 A1* | 11/2006 | Gardner, Jr. ....... G01N 21/6456 356/301 |
| 2008/0273208 A1 | 11/2008 | Johansen et al. |
| 2013/0293893 A1 | 11/2013 | Bonyuet et al. |

OTHER PUBLICATIONS

International Search Report and Written Opinion for PCT/US2009/041254, dated Oct. 9, 2009 (16 pages).

International Preliminary Report on Patentability for PCT/US2009/041254, mailing date Feb. 10, 2011 (9 pages).

Saptari et al., Design of a mechanical-tunable filter spectrometer for noninvasive glucose measurement, Applied Optics 43(13): 1 (2004).

\* cited by examiner

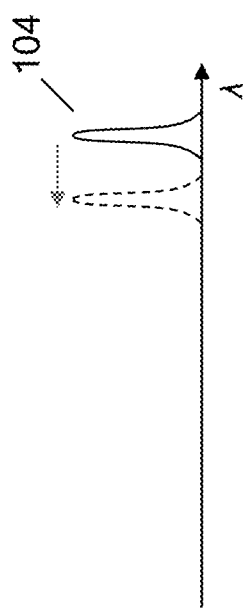
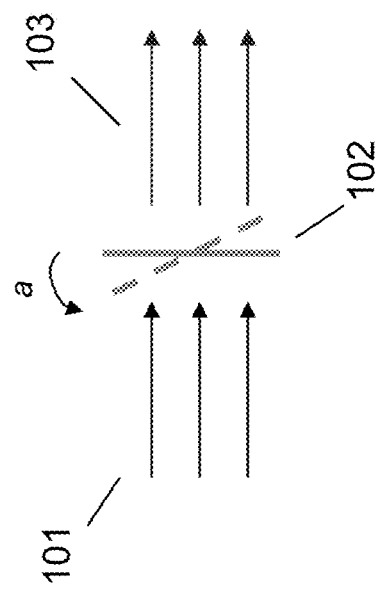
FIG. 1

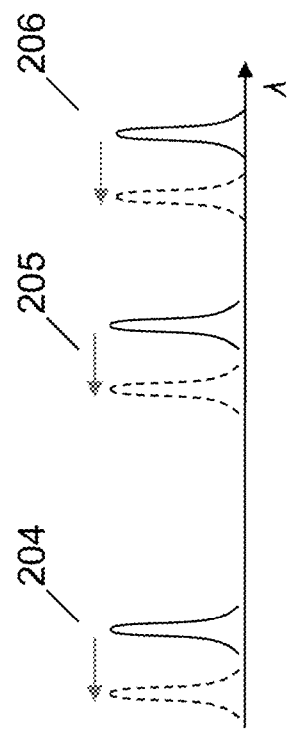
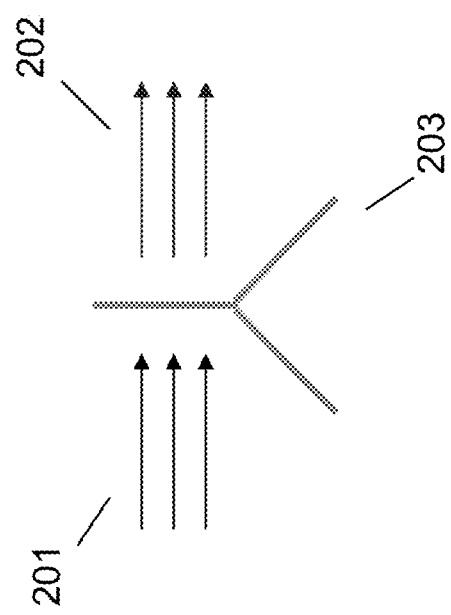
FIG. 2

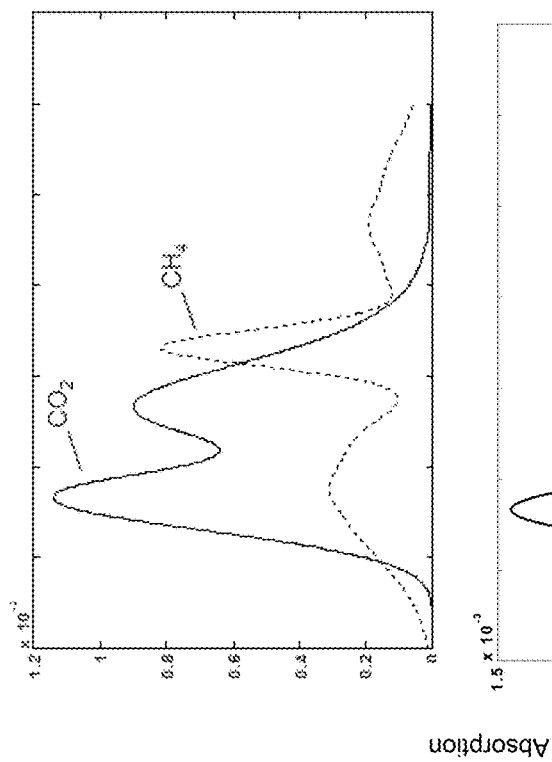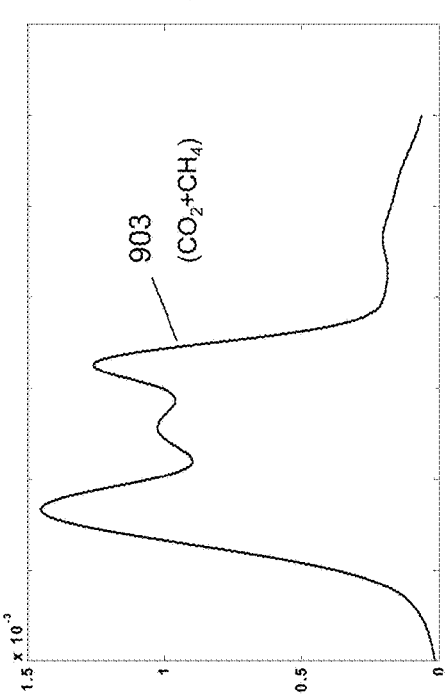

MULTIPLEX TUNABLE FILTER SPECTROMETER

RELATED APPLICATIONS

The present application is a continuation of U.S. patent application Ser. No. 12/755,980, filed Apr. 7, 2010, now U.S. Pat. No. 8,896,839, which claims the benefit of (priority to) U.S. Provisional Patent Application No. 61/212,165, filed Apr. 8, 2009, entitled, "Multiplex Tunable Filter Spectrometer," by Saptari, the text of which is hereby incorporated herein by reference, in its entirety. Also incorporated herein by reference in its entirety is the text of International (PCT) Patent Application No. PCT/US09/41254, filed Apr. 21, 2009, and published on Feb. 4, 2010, as WO 2010/014277.

FIELD OF THE INVENTION

The invention relates generally to spectroscopic systems and spectrometers. More particularly, in certain embodiments, the invention relates to methods and systems for measuring and/or monitoring the chemical composition of a sample (e.g., a process stream), and/or detecting substances or compounds in a sample, using light spectroscopy. More particularly, in certain embodiments, the invention relates to a multiplex, wavelength-scanning, interference filter based optical spectrometer.

BACKGROUND OF THE INVENTION

Optical spectrometers are systems that enable the measurement of optical intensity at specific wavelengths or spectral bands. Optical spectrometers are used in some chemical or biological analysis devices or analyzers to detect, identify and/or quantify chemical or biological species. Absorption, Raman and fluorescence spectroscopy are some of the most common methods used to optically analyze chemical or biological samples. Several commonly used optical spectrometers today include Fourier-transform spectrometers (FTS), grating based spectrometers being the most common dispersive type of spectrometer, and filter based spectrometers that employ a linear variable filter (LVF)—e.g., as described in U.S. Pat. No. 5,166,755 to Gat; U.S. Pat. No. 5,218,473 to Seddon et. al.; and U.S. Pat. No. 6,057,925 to Anthon, the texts of which are incorporated herein by reference, in their entirety—and angularly tuned filter spectrometers—e.g., as described in U.S. Pat. No. 4,040,747 to Webster; U.S. Pat. No. 2,834,246 to Foskett; U.S. Pat. No. 5,268,745 to Goody; and U.S. Pat. No. 7,099,003 to Saptari, the texts of which are incorporated herein by reference, in their entirety.

Many chemical and biological analyses today require high sensitivity devices, measuring trace components very accurately and reproducibly, down to parts-per-million or even parts-per-billion levels. As such, optical spectrometers with high optical throughput or etendue are essential. Fourier transform spectrometers and angle-tuned filter spectrometers, in principle, can provide the required high optical throughput, whereas dispersive spectrometers provide relatively much lower throughput. In addition, many chemical and biological analyses require multiple and/or wide spectral or wavelength coverage due to the need to measure multiple species and/or the need to compensate for signal interferences arising from the presence of other species in the sample.

Although Fourier transform spectrometers can in principle provide high throughput or etendue capability, they require complex instrumentation, including high-precision optical components and subassemblies, and thus are relatively expensive and cumbersome to operate and maintain. Rotating filter spectrometers, such as those described in U.S. Pat. No. 4,040,747 to Webster; U.S. Pat. No. 5,268,745 to Goody; and U.S. Pat. No. 7,099,003 to Saptari, can provide as high throughput as Fourier transform spectrometers without the instrumentation complexity of the FTS. However, the tilting or rotating filter spectrometers provide rather limited wavelength coverage, for example, approximately, 1-5% of the nominal wavelength of the filter, corresponding to an effective angular scan distance of approximately 0-60 degrees, due to geometrical limitations (zero degree refers to zero degree of incident angle).

Systems employing a plurality of filters have been described and are reported to include additional wavelength bands and/or extend the wavelength coverage. See, e.g., U.S. Pat. No. 4,040,747 to Webster; and U.S. Pat. No. 7,099,003 to Saptari. However, such systems provide additional wavelength bands by adding filters that are scanned in series, i.e. one wavelength band is scanned at a time. With such systems, the number of wavelength bands that can be covered by the system is limited geometrically by the rotating assembly design. For example, with a single rotation axis and a single rotation assembly, the maximum practical number of filters, and thus wavelength bands, is three (e.g., see U.S. Pat. No. 4,040,747 to Webster; and U.S. Pat. No. 7,099,003 to Saptari). Additional bands may be achieved through the use of additional filter assemblies and/or axes of motion. However, such additions would further complicate the system instrumentation. In addition, such filter spectrometers do not exhibit the multiplex advantage of FTS, i.e. being able to measure the analysis wavelength bands simultaneously, which provides a further improved sensitivity performance. There is a need for a spectrometer that provides the multiplex advantage of FTS, with reduced instrumentation complexity.

SUMMARY OF THE INVENTION

Presented herein is a compact, rugged, inexpensive spectroscopic system well-suited for industrial applications. The system features a spectrometer that enables high etendue or high optical throughput spectroscopic measurement, wavelength band multiplexing capability, and reduced system complexity compared to FTS systems. The system may be used to perform spectroscopic determinations of chemical and/or biological media. For example, the system may be used to determine media composition, detect the presence or absence of certain species or analytes, determine the concentration of one or more species in a sample, and/or to verify sample quality and consistency with a known set of samples.

In preferred embodiments, the spectrometer features a rotatable or tiltable filter assembly comprising one or more multi-band optical bandpass interference filter(s). Because the moving filters have multiple wavelength bands, multiple wavelength sweeps can be performed simultaneously, providing improved sensitivity and versatility. Light that strikes a filter within the bandpass wavelength regions is transmitted through the filter, and the light outside the bandpass regions is reflected back. Through a rotary motion of the filter assembly, continuous wavelength sweeping within multiple wavelength regions is performed simultaneously. The rotary motion produces varying incident angle at which light strikes the surface of the filter module. The multi-band filter module may be constructed from multiple bandpass filters mechanically joined together. The multi-band filter module may alternatively be constructed from a single filter element specifically designed to transmit multiple bandpass regions.

In certain embodiments, the invention provides a spectroscopic system and method wherein selected wavelength-swept regions provide spectral analysis of the target chemical or biological species in a sample, as well as orthogonal analysis of spectral interferences arising from the background media or other existing or potentially existing species. In certain embodiments, some of wavelength-swept regions are selected to provide compensation for ambient and/or sample conditions such as temperature and pressure.

Multiple spectral features arising from interaction of the light with the target analytes may result in overlapping spectral features. In preferred embodiments, the spectrum of the individual target analyte is extracted or separated by using chemometrics such as multiple linear regression, principal components analysis or partial least squares.

In certain embodiments, the spectroscopic system of the present invention includes an electromagnetic radiation source (e.g., a light source), a detector for receiving light, and a filter based spectrometer. The light source may include a blackbody emitter, LED or SLED (super light-emitting diode) sources, a flashlamp, an arc lamp, or light emitted from natural sources such as the sun or other heat sources. The detector may include a photodiode, a thermal based detector such as pyroelectric detector, or a photomultiplier tube.

In one aspect, the invention is directed to a spectroscopic system including: (i) an optical filter module which includes one or more optical interference filters configured to receive electromagnetic radiation from an electromagnetic radiation source, the one or more filters having a plurality of multiplexed bandpass regions configured to simultaneously transmit multiple wavelength bands of electromagnetic radiation through the filter module; and (ii) an optical detector configured to receive the multiple wavelength bands of electromagnetic radiation transmitted through the filter module and to generate one or more electrical signals indicative of electromagnetic radiation intensity as a function of wavelength.

In certain embodiments, the filter module includes an interference filter comprising multiple bandpass regions. The filter module may also or alternatively include a plurality of interference filters which individually or collectively comprise multiple bandpass regions.

In certain embodiments, the optical filter module is configured to provide adjustment of the incident angle of the electromagnetic radiation from the electromagnetic radiation source onto the one or more optical filters. The optical filter module may include a rotatable filter assembly to provide the incident angle adjustment. The rotatable filter assembly may include a position detector to produce at least a first signal comprising a series of digital pulses corresponding to the angular position of the rotatable filter assembly. The position detector may be configured to clock analog-to-digital conversion. In certain embodiments, the rotatable filter assembly includes at least four multiplexed bandpass regions on a single rotatable filter assembly with a single rotation axis.

In certain embodiments, the spectroscopic system further includes a memory for storing code that defines a set of instructions (e.g., software); and a processor for executing the set of instructions to identify one or more species present in a sample from which the electromagnetic radiation emanates or through which the electromagnetic radiation passes prior to reception by the optical detector. The software may direct the processing of data corresponding to the electromagnetic radiation intensity measured by the detector over the multiple wavelength bands, thereby (i) identifying one or more species present in the sample, (ii) quantifying each of one or more species present in the sample (e.g., determining concentrations or densities), (iii) identifying the absence of one or more species for which the sample is tested, or (iv) any combination of the above.

In certain embodiments, the optical detector is configured to receive the multiple wavelength bands of electromagnetic radiation after transmission through both the filter module and a sample being measured. The system may further include a sample cell configured to contain a sample through which the electromagnetic radiation passes or from which the electromagnetic radiation emanates prior to reception by the optical detector. The sample cell may be located upstream or downstream of the optical filter module.

In certain embodiments, the optical detector, in conjunction with the optical filter module, is configured to generate one or more electrical signals indicative of electromagnetic radiation intensity over a sweep of wavelengths within each of the multiple wavelength bands.

In certain embodiments, the spectroscopic system further includes the electromagnetic radiation source. The electromagnetic radiation source may produce visible light, infrared light, near-infrared light, and/or ultraviolet light.

In another aspect, the invention is directed to a spectroscopic method for detecting and/or quantifying one or more species in a sample, the method comprising the steps of: (a) directing electromagnetic radiation from an electromagnetic radiation source into an optical filter module comprising one or more optical interference filters, the one or more optical filters comprising a plurality of multiplexed bandpass regions configured to transmit multiple wavelength bands of electromagnetic radiation through the filter module simultaneously; (b) directing the multiple wavelength bands of electromagnetic radiation through a sample comprising one or more species; (c) directing the multiple wavelength bands of electromagnetic radiation from the sample into an optical detector configured to generate one or more electrical signals indicative of electromagnetic radiation intensity over a sweep of wavelengths within each of the multiple wavelength bands; and (d) processing data corresponding to the one or more electrical signals to identify and/or quantify one or more species present in the sample.

Elements of embodiments described with respect to a given aspect of the invention may be used in various embodiments of another aspect of the invention. For example, elements of the various embodiments of the spectroscopic system described herein may be used in the spectroscopic method described herein, and vice versa.

BRIEF DESCRIPTION OF DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1 is an illustration of a tunable filter spectrometer using a rotating filter.

FIG. 2 is an illustration of a tunable filter spectrometer using a plurality of single-band rotating filters.

FIGS. 9A and 9B are graphs showing individual gas sample spectra and the combined gas sample spectrum as measured by a multiplex filter spectrometer, according to an illustrative embodiment of the invention.

DETAILED DESCRIPTION

Figure 3:
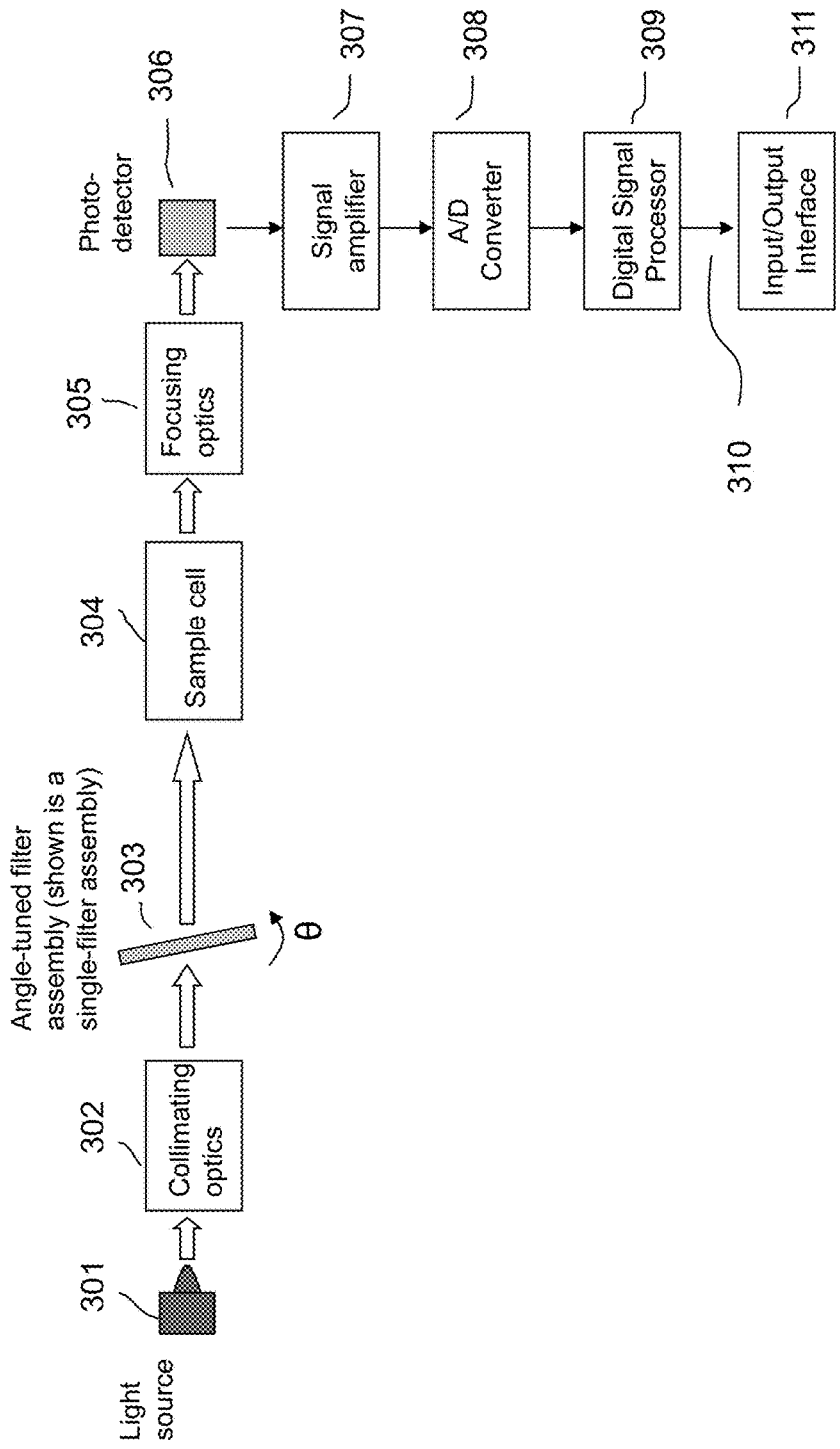
FIG. 3 is an illustration of a system block diagram of a spectrometer system, according to an illustrative embodiment of the invention.

It is contemplated that methods, systems, and processes described herein encompass variations and adaptations developed using information from the embodiments described herein.

Throughout the description, where systems and apparatus are described as having, including, or comprising specific components, or where processes and methods are described as having, including, or comprising specific steps, it is contemplated that, additionally, there are systems and apparatus of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

FIG. 1 is an illustration of a tunable filter spectrometer using a rotating filter 102. The filter 102 rotates as shown as light 101 from a light source passes through the filter 103, thereby shifting the wavelength 104 of the filter. FIG. 2 illustrates a tunable filter spectrometer using three single-band rotating filters, where the filter module 203 rotates as light 201 from a light source passes through the three filters of the filter module 203, thereby shifting the wavelengths 204, 205, 206 of the filters. The wavelength bands are scanned in series, i.e. one wavelength band is scanned at a time. With such systems, the number of wavelength bands that can be covered by the system is limited geometrically by the rotating assembly design. For example, with a single rotation axis and a single rotation assembly, the maximum practical number of filters, and thus wavelength bands, is three.

FIG. 3 is a block diagram of hardware components of a spectroscopic system featuring a multi-band angle-tuned filter spectrometer, according to an illustrative embodiment of the invention. Starting from the left on the diagram, the system includes a light source 301 that contains the plurality of wavelengths to be analyzed. In the case of absorption measurement, the light source 301 would contain the wavelengths at which the sample is 'active' or absorbing light. The light source 301 may be a filament based or a light emitting diode source, for example. In the case of emission spectroscopic measurement such as Raman or fluorescence spectroscopy, the light source is the emitted light radiation from the sample. A collimating optics assembly 302 is generally needed to control the degree of collimation of the light prior to entering the filter assembly. The collimating optics assembly may include one or multiple lenses or mirrors and apertures. The filter assembly 303 comprises the multi-bandpass filter and its electro-mechanics used to control its angular motion. The motion may be a continuous rotation, a back-and-forth tilt or a step-scan motion covering the full angular distance needed. The amount of angular distance needed depends on the required wavelength scan range. The angular distance is generally between +/−30 degrees to +/−60 degrees, but values outside these bounds are possible. The sample cell 304 holds the sample to be analyzed, which may be in gaseous, liquid, slurry or solid form. The configuration as shown with the sample cell located downstream of the filter assembly is typical for an absorption measurement. In the case of emission measurement, such as Raman or fluorescence spectroscopy, the sample cell would be upstream of the filter assembly and the light source 301 in FIG. 3 would represent the light emitted from the sample itself. The focusing optics assembly 305 is configured to focus the light onto a photodetector 306 element, which generally needs to be made small to provide the required signal-to-noise ratio for quantitative analysis. The size of the detector's active area is generally on the order of 1 mm$^2$ or smaller, where the beam size is generally on the order ten millimeters or larger. The focusing optics 305 may include one or more lenses and/or mirrors. The function of the photo-detector 306 is to convert the light radiation into electrical signal. Different types of photo-detectors may be used, depending on the regions of the spectrum being analyzed. For example, in the visible region, silicon photo-detector is popularly used, whereas in the infrared region, Indium Gallium Arsenide (InGaAs), Indium Arsenide (InAs), Mercury Cadmium Telluride (MCT) and pyroelectric based detectors are available as options. The signal amplifier 307 amplifies and/or conditions the electrical output of the photo-detector 306 to the appropriate types and/or levels for input to the analog-to-digital converter (ADC) 308. The digital signal processor (DSP) 309 contains an algorithm that speciates or decodes the encoded multi-band and multi-component spectra into the individual species components in the sample being analyzed. The DSP 309 may also contain an algorithm that computes the quantitative levels of the sample components. The DSP may be implemented on an external computer, on an on-board computer or on a fully embedded microprocessor. The DSP algorithm may be composed of various types of algorithms including least-squares based chemometrics such as classical least squares (CLS) or principal component analysis (PCA) in which the measured spectra are modeled or fitted against pre-established calibration spectra or other types of pattern recognition algorithm utilizing any of the spectral features. The output of the DSP, 310, may include quantitative information of the sample components, whether it is in concentration, density or other appropriate measurement units depending on the application. The DSP output 310 may also contain other relevant measurement or system information such as system health indicators, measurement confidence levels and other auxiliary measurements such as sample pressure and temperature. The input/output interface 311 provides the necessary interfaces to transmit the measurement outputs to the user or to other machineries. In addition, the input/output interface may also connect with user input devices to provide the ability to make changes to configurable parameters such as update rate, signal averaging time and data logging parameters.

Figure 4B:
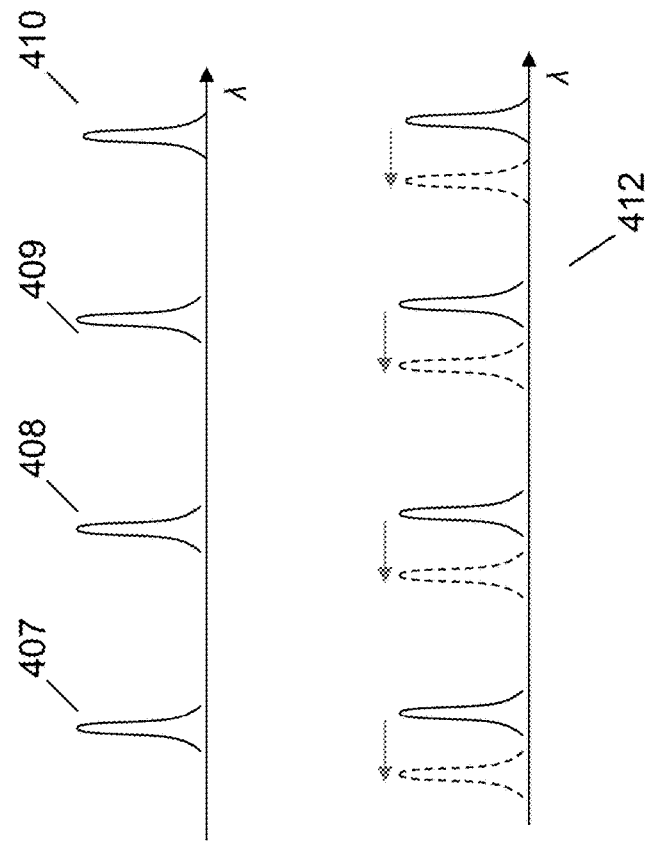
FIG. 4B is a graph showing spectroscopic data corresponding to each of the multiple bandpass filters of the multiple filter module of FIG. 4A, according to an illustrative embodiment of the invention.
Figure 4A:
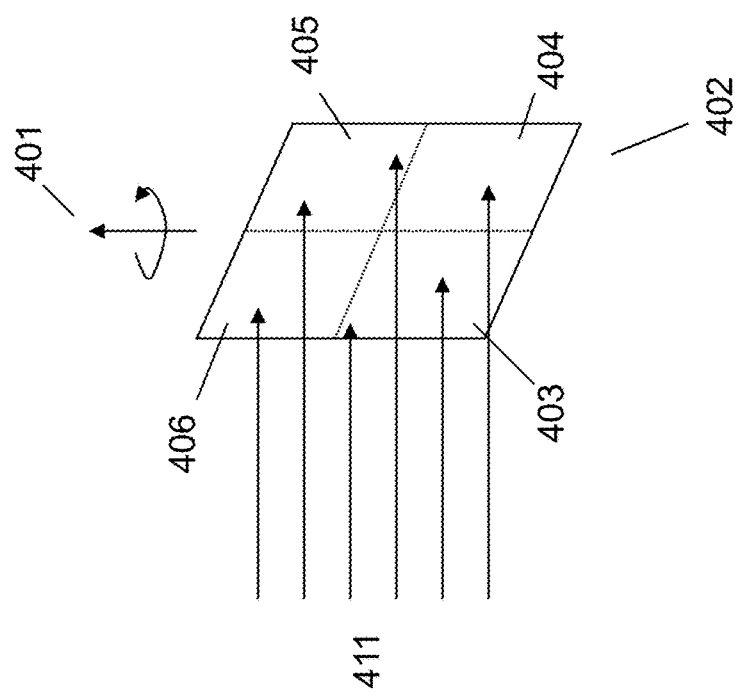
FIG. 4A is a schematic illustration of a multiplex filter module comprising multiple bandpass filters, configured to mount in a plane and rotate on its center axis, according to an illustrative embodiment of the invention.

FIGS. 4A and 4B illustrate a filter assembly which allows for simultaneous multi-band or multiplexed wavelength scanning. In this particular embodiment, the filter module 402 is composed of four bandpass filters 403, 404, 405 and 406, each transmitting a particular wavelength region, 407, 408, 409 and 410 respectively at zero incident angle between the light beam as illustrated by light ray 411 and the surface of the filter module. As the filter module 402 rotates about the rotation axis 401 away from zero incident angle, the bandpass region of each filter is shifted to a shorter wavelength as illustrated by diagram 412. In certain embodiments, the incident angle is varied by continuous rotation of the filter module in a particular direction, either clockwise or anti-clockwise. In certain embodiments, the filter module is rotated back-and-forth periodically. In certain other embodiments, the filter module rotates in a step-and-scan mode, where it rotates to a certain angular position, stops, and collects data, and does this repetitively until the full angular distance is covered.

Figure 5B:
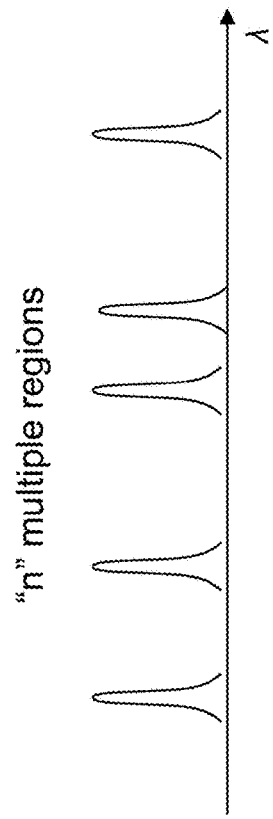
FIG. 5B is a graph showing spectroscopic data corresponding to each of the multiple bandpass regions of FIG. 5A, according to an illustrative embodiment of the invention.
Figure 5A:
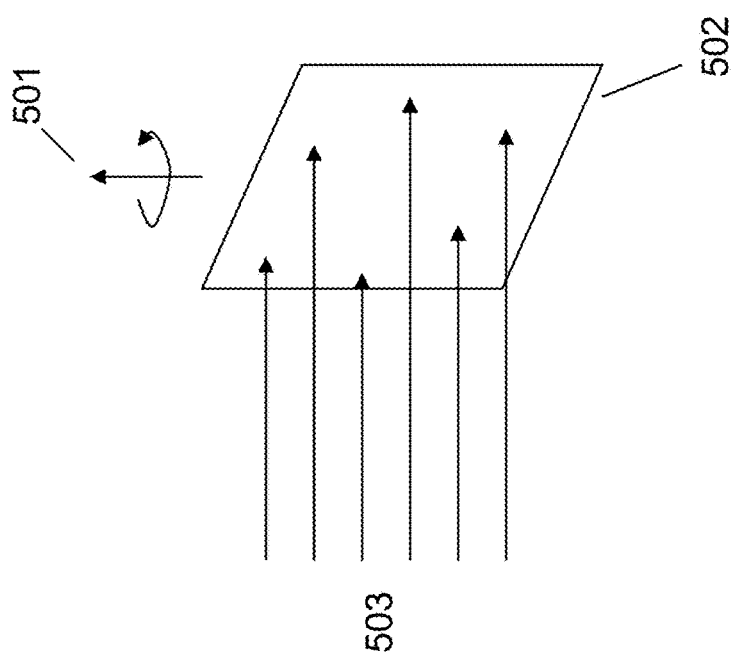
FIG. 5A is a schematic illustration of a filter module comprising a single filter element producing multiple bandpass regions, according to an illustrative embodiment of the invention.

In certain embodiments, the filter module is composed of a single interference filter element that is specifically made to transmit more than one bandpass region. FIG. 5 shows an illustration of a custom interference filter 502, which provides multiple bandpass regions. When rotated about axis 501, the incident angle of the light beam 503 varies. As a result, each of the "n" bandpass functions shifts with respect to wavelength.

Figure 6B:
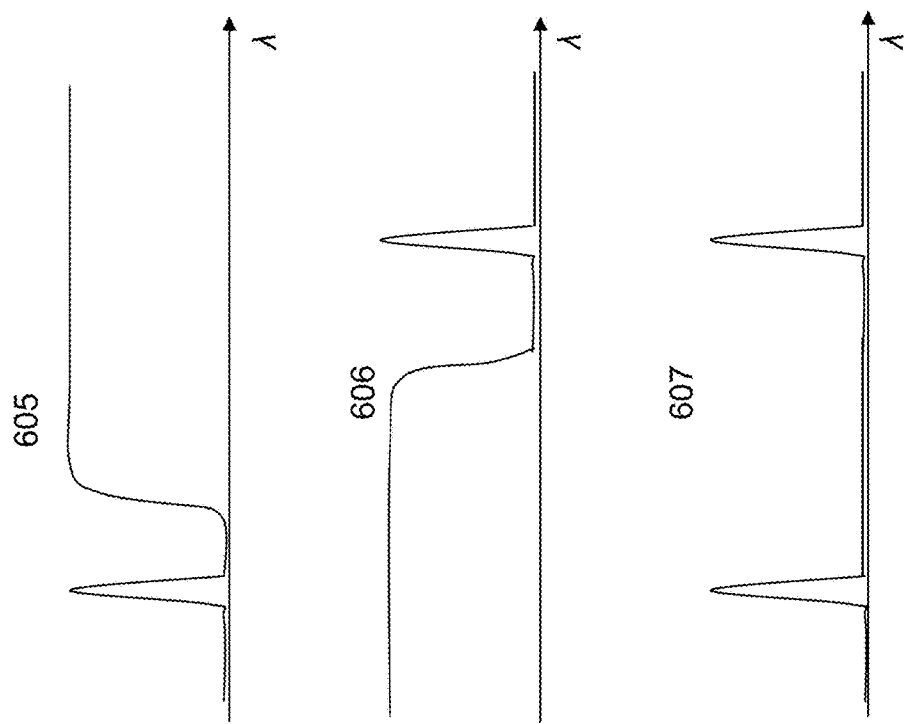
FIG. 6B is a graph showing spectroscopic data corresponding to the multiple bandpass regions of the stacked filter elements of FIG. 6A, according to an illustrative embodiment of the invention.
Figure 6A:
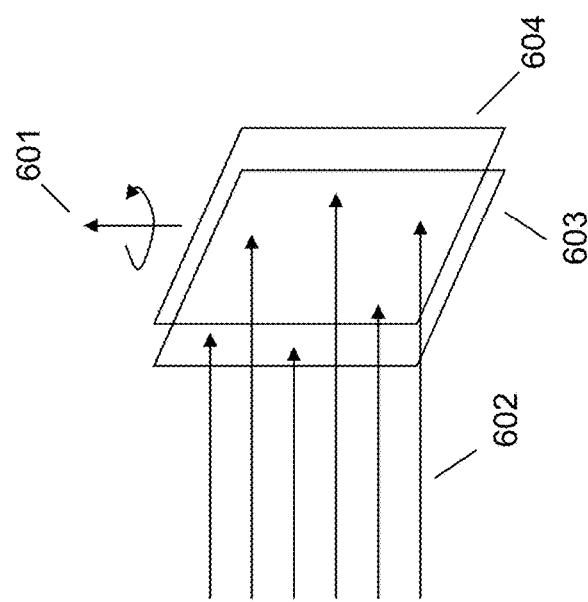
FIG. 6A is a schematic illustration of a filter module comprising stacked filter elements, according to an illustrative embodiment of the invention.

In certain embodiments, the filter module is composed of multiple stacked interference filters, with a combined effective transmission function comprising multiple bandpass regions, as illustrated in FIG. 6. In this illustration, two filters 603 and 604 are stacked. Each filter has a transmission function comprising a bandpass and an edgepass (long-wave or short-wave pass transmission functions), as illustrated by diagrams 605 and 606. The combined effective transmission function of the stacked filter module is illustrated by diagram 607.

In certain embodiments, the filter module is composed of more than one multi-band filters rotated or tilted in series, creating a total of m×n band regions, where m is the number of the multi-band filters and n is the number of bands per filter. The number of bands on each filter does not necessarily have to be equal to each other. For example, a filter may contain two bands while another contains four. The purpose of this configuration would be to further increase the number of bands beyond what is practically achievable through the use of a single multi-band filter without any additional rotary axes. The practical limitations to the number of bands of a single filter include the filter design/fabrication complexity, manufacturing cost and reduction in the effective optical throughput per band.

Figure 7:
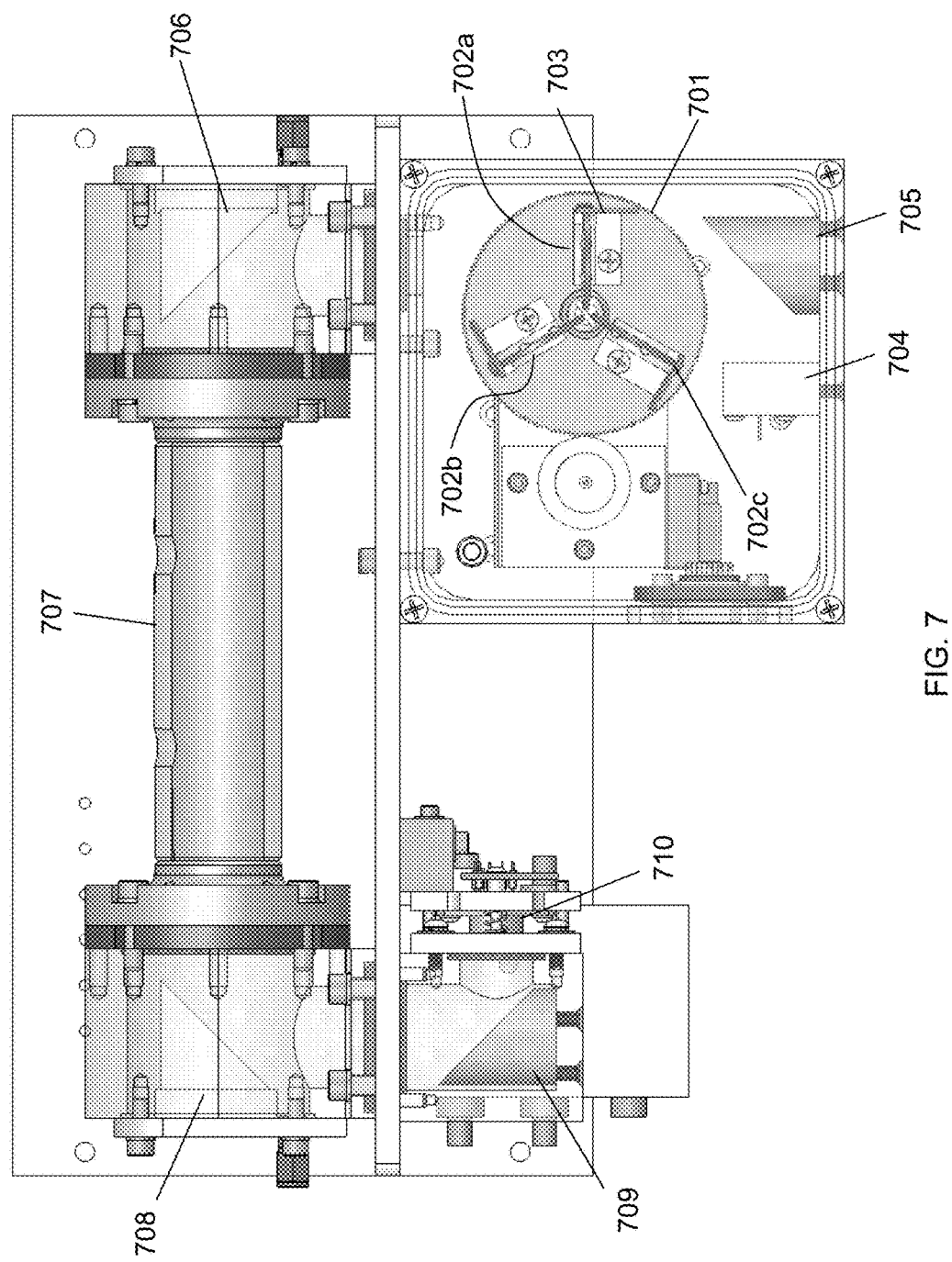
FIG. 7 is a schematic drawing of a spectroscopic system and optical layout of a spectrometer, according to an illustrative embodiment of the invention.

FIG. 7 illustrates a hardware implementation of a system design utilizing three multi-band filters as its filter spectrometer assembly. The rotary assembly 701 comprises three multi-band filters 702a, 702b and 702c. Each of the individual multi-band filters may be constructed from joined filters as illustrated in FIG. 4, or may be a custom designed filter as illustrated in FIG. 5, or may comprise stacked filters as illustrated in FIG. 6. Filter shields 703 are used to block the light at certain potions of the rotation where part of the light is not incident on any of the filters, thereby preventing detector saturation. The light source assembly 704 may be made of various types of emitters including filament based emitters and LED emitters. In this design, a 90-degree parabolic mirror 705 is used to collimate the light and direct it to the filter assembly. The light beam is directed into the sample cell 707 by the 90-degree flat mirror 706. Upon exiting the sample cell, the light beam is reflected at another 90-degree flat mirror 708, which is then directed and focused by another parabolic mirror 709 onto a photo-detector 710.

Non-limiting examples of approximate wavelength ranges for infrared filters that may be used with the spectroscopic systems described herein include the following: 2600-2720 nm for moisture and $CO_2$ analysis; 3250-3420 nm for hydrocarbon gas analysis; 4400-4720 nm for CO analysis; 1600-1780 nm for hydrocarbon gas analysis; and 1625-1800 nm for alcohol-water liquid analysis. Non-limiting examples of approximate wavelength ranges for UV filters that may be used with the spectroscopic systems described herein include the following: 180-210 nm for $H_2S$ analysis; and 200-230 nm for sulfur analysis in natural gas. A non-limiting example of an approximate wavelength range for visible light filters that may be used with the spectroscopic systems described herein is 750-780 nm for $O_2$ analysis.

Figure 8:
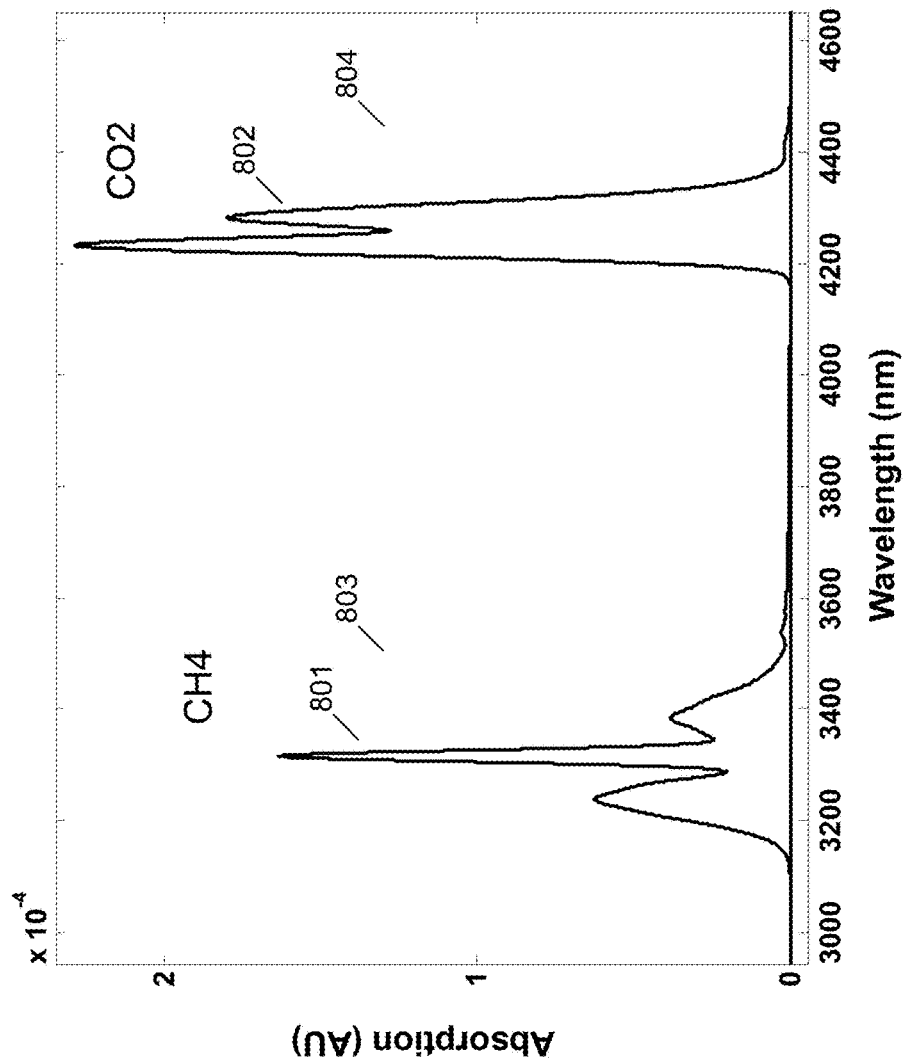
FIG. 8 is a graph showing exemplary absorption spectra of CO2 and CH4 gases that may be obtained using a spectroscopic system with multiple bandpass regions, according to an illustrative embodiment of the invention.

The following constructive example illustrates the mechanism by which the spectrometer provides multiplexed spectral analysis. Consider the measurement of carbon dioxide ($CO_2$) gas and methane ($CH_4$) gas, two important compounds in pollution/environmental studies and combustion control and analysis. FIG. 8 shows the absorption spectra of CH4 (801) and $CO_2$ gases (802). The filter module is designed such that through the effective angular sweeping distance, the bandpass functions of the filter module sweep through the appropriate features of the gases. In this case, the filter module is designed such that it sweeps through bandpass regions within approximately 3100-3500 nm region for the CH4 analysis and 4100-4500 nm region for the $CO_2$ analysis as indicated by the shaded regions 803 and 804 respectively. An absorption spectrum of a mixture of the gases $CO_2$ and $CH_4$ analyzed by the spectrometer would result in a blended spectrum as simulated and illustrated in FIG. 9, specifically in 902. The graphs shown in 901 illustrate the simulated individual absorption spectra the spectrometer would generate, i.e. when pure gaseous sample of each compound enters the sample cell.

The determination of the number of analyzed wavelength bands and the specific locations of the bands is dependent upon the application or measurement criteria. The spectrometer system may be configured to include a particular wavelength band to enable measurement of the target compound that is active in that region. Following the measurement example above, the two wavelength bands 803 and 804 as shown in FIG. 8 are selected to enable the measurement of $CO_2$ and $CH_4$ target compounds. In another case, a wavelength band may be included to allow for compensation of an interfering background compound. For example, in combustion gas measurement where moisture is abundant in the sample stream, there may be measurement problems for some target gases including NO and $NO_2$, due to spectral interferences. Although moisture is not a target compound, a wavelength band where only moisture is active may be included so it can be measured and used to correct for the errors due to the spectral interferences.

Figure 10:
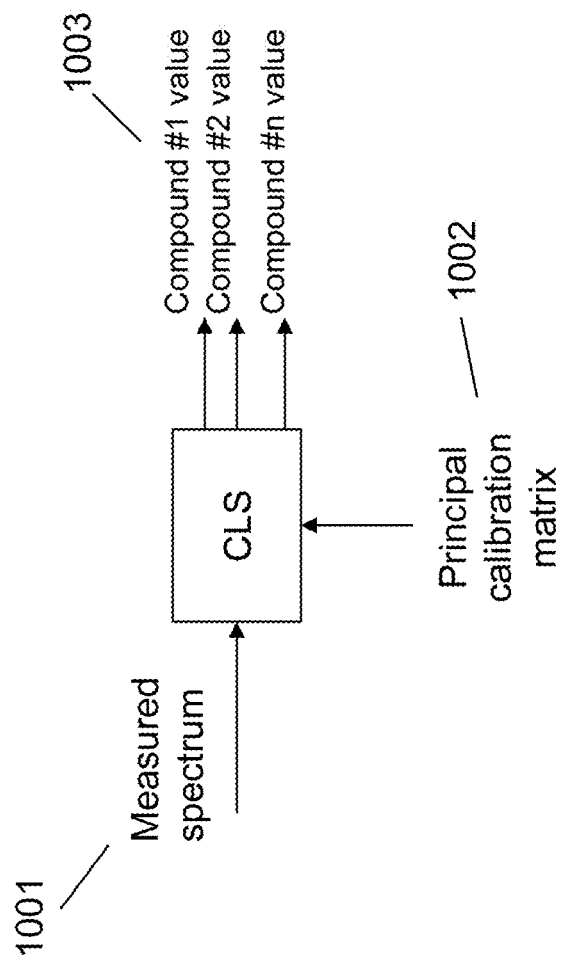
FIG. 10 is a block diagram of a CLS based processing algorithm, according to an illustrative embodiment of the invention.

The digitized, wavelength multiplexed spectral information would then be processed to separate the spectrum into the individual compound spectrum, which is then compared against a calibrated spectrum to produce its concentration or density value. This may be accomplished through different types of algorithms including least-squares based chemometrics such as classical least squares (CLS) or principal component analysis (PCA). Following the above example, FIG. 10 is block diagram of a CLS based processing algorithm to speciate and quantify the individual concentrations of the gases. The measured spectrum 1001 is modeled or fitted against the principal calibration matrix 1002 containing calibrated spectra of the individual sample through a least-squares regression algorithm. In the constructive example above, the calibration matrix 1002 would contain a calibrated spectrum of $CO_2$ and a calibrated spectrum of $CH_4$. The outputs of the algorithm, 1003, would include the quantitative values of the individual samples, such as concentration or density values.

Figure 11B:
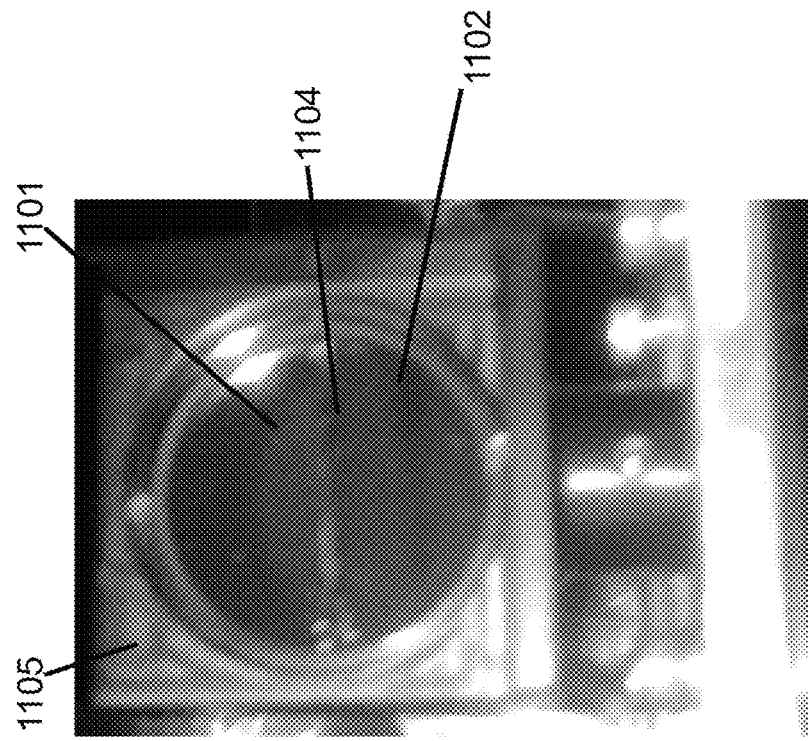
FIG. 11B is a photograph of the filter module of FIG. 11A, according to an illustrative embodiment of the invention.
Figure 11A:
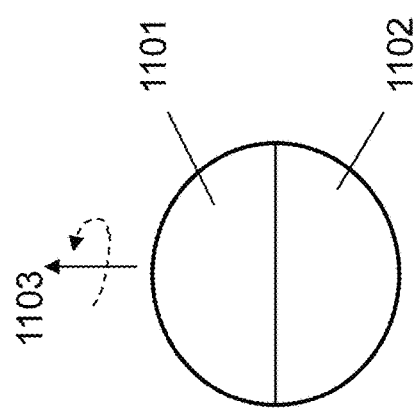
FIG. 11A is a schematic drawing of a filter module of a prototype spectrometer, the filter module comprising a two-band filter that rotates about the axis shown, according to an illustrative embodiment of the invention.

A prototype spectrometer was built and tested to further illustrate the multiplexed spectral measurement. The prototype unit uses a two-band filter, constructed from two separate narrow band-pass filters made by Spectrogon US Inc, Parsippany, N.J. The filter assembly as depicted in FIG. 11A (diagram) and FIG. 11B (photograph) is composed of two D-shaped filters 1101 and 1102 joined together. In this prototype, element 1101 is a narrow band-pass filter with a nominal peak wavelength at 4370 nm (Spectrogon filter part no. NB-4370-020 nm) suitable for $CO_2$ measurement and element 1102 is a narrow band-pass filter with a nominal peak wavelength at 3520 nm (Spectrogon filter part no. NB-3520-020 nm) suitable for $CH_4$ measurement. In this prototype, the two filters are joined together using silicon adhesive as shown by the apparent adhesive line 1104 and then ring-mounted on a hard plastic mount 1105.

Figure 12:
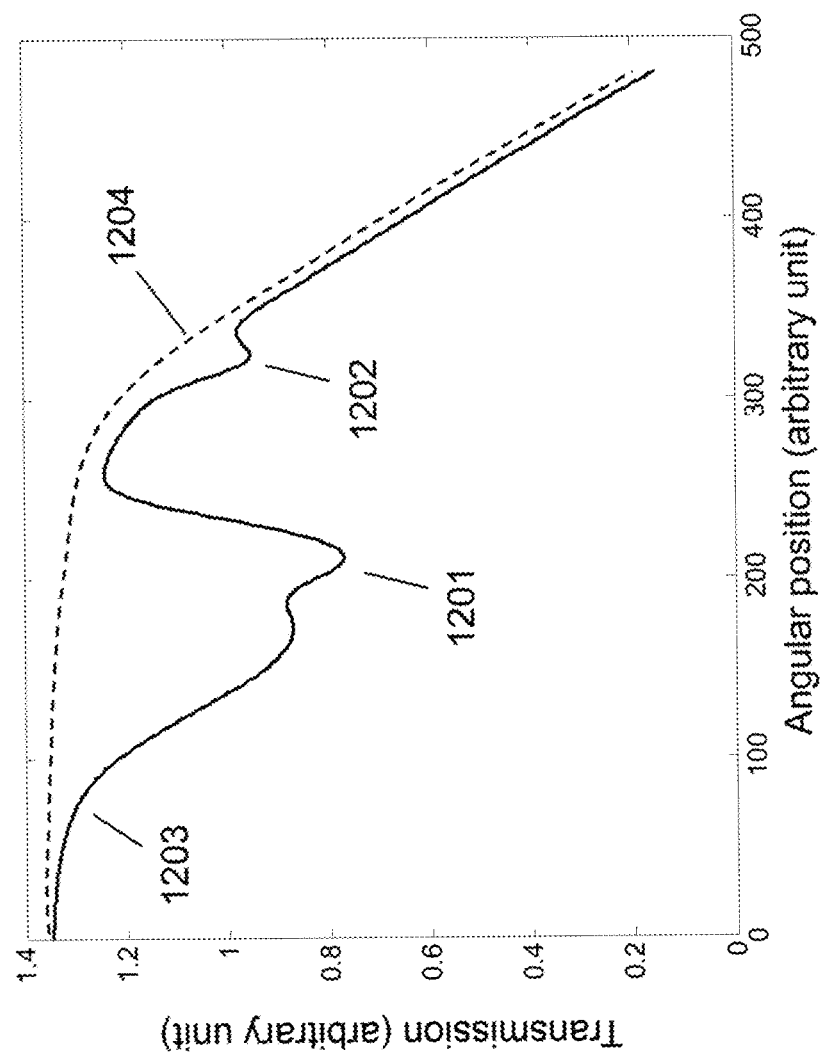
FIG. 12 is a graph showing an experimentally measured transmission spectrum using the filter module of FIG. 11A, 11B, according to an illustrative embodiment of the invention.

FIG. 12 shows an experimentally measured single-beam or transmission spectrum 1203 of the spectrometer when measuring a mixture of $CO_2$ and $CH_4$ gases. The absorption peak 1201 corresponds to a $CO_2$ absorption peak and the absorption peak 1202 corresponds to a $CH_4$ absorption peak. The transmission spectrum 1204 is a transmission spectrum from a measurement of a background zero gas, which in this case is nitrogen. In this spectrum, no absorption peaks are present since nitrogen is not infrared active and therefore is suitable to use to obtain a zero reference.

Figure 13:
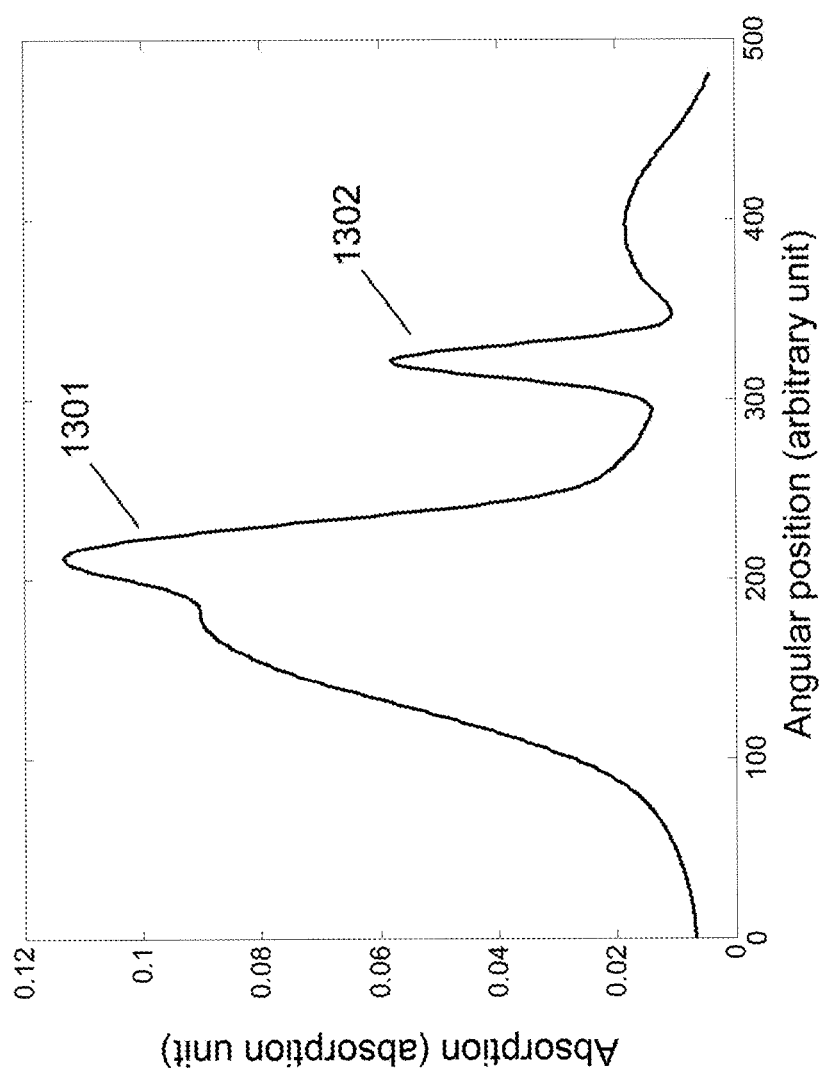
FIG. 13 is a graph showing an experimentally measured absorption spectrum using the filter module of FIG. 11A, 11B, according to an illustrative embodiment of the invention.

FIG. 13 shows the absorption spectrum of the above measurement. The absorption spectrum is obtained by taking a logarithm of the ratio of the zero gas transmission spectrum 1204 and the gas mixture transmission spectrum 1203. This absorption spectrum more clearly shows the absorption peak due to $CO_2$ absorption 1301 and the absorption peak due to $CH_4$ absorption 1302. In particular, the $CO_2$ absorption peak 1301 is spectrally located at around 4230 nm and the $CH_4$ absorption peak 1302 is spectrally located at around 3310 nm (the spectra in wavelength scale are shown in FIG. 8). The above experimental measurement demonstrates the capability of the spectrometer in gathering spectra from multiple wavelength bands simultaneously.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A spectroscopic method for detecting and/or quantifying one or more species in a sample, the method comprising the steps of:
    directing electromagnetic radiation from an electromagnetic radiation source into an optical filter module comprising one or more optical interference filters, the one or more optical filters comprising a plurality of multiplexed bandpass regions configured to transmit multiple wavelength bands of electromagnetic radiation through the filter module simultaneously;
    directing the simultaneously transmitted multiple wavelength bands of electromagnetic radiation through a sample comprising one or more species;
    directing the simultaneously transmitted multiple wavelength bands of electromagnetic radiation from the sample into an optical detector;
    generating, by the optical detector, one or more electrical signals indicative of electromagnetic radiation intensity over a sweep of wavelengths within each of the multiple wavelength bands;
    continuously sweeping the plurality of multiplexed bandpass regions to produce data corresponding to the one or more electrical signals; and
    processing the data corresponding to the one or more electrical signals to identify and/or quantify one or more species present in the sample.

2. The spectroscopic method of claim 1, wherein the optical filter module comprises an interference filter comprising multiple bandpass regions.

3. The spectroscopic method of claim 1, wherein the optical filter module comprises a plurality of interference filters which collectively comprise the multiple bandpass regions.

4. The spectroscopic method of claim 1, wherein the optical filter module adjusts an incident angle of the electromagnetic radiation from the electromagnetic radiation source onto the one or more optical filters.

5. The spectroscopic method of claim 4, wherein the optical filter module comprises a rotatable filter assembly that adjusts the incident angle.

6. The spectroscopic method of claim 5, wherein the rotatable filter assembly comprises a position detector that produces at least a first signal comprising a series of digital pulses corresponding to the angular position of the rotatable filter assembly.

7. The spectroscopic method of claim 6, wherein the position detector clocks analog-to-digital conversion.

8. The spectroscopic method of claim 5, wherein the rotatable filter assembly comprises at least four multiplexed bandpass regions on a single rotatable filter assembly with a single rotation axis.

9. The spectroscopic method of claim 1, comprising:
identifying, by a processor, one or more species present in a sample from which the electromagnetic radiation emanates or through which the electromagnetic radiation passes prior to reception by the optical detector.

10. The spectroscopic method of claim 9, comprising:
processing, by the processor, data corresponding to the electromagnetic radiation intensity measured by the detector over the multiple wavelength bands, thereby identifying one or more species present in the sample.

11. The spectroscopic method of claim 9, comprising:
processing, by the processor, data corresponding to the electromagnetic radiation intensity measured by the detector over the multiple wavelength bands, thereby quantifying each of one or more species present in the sample.

12. The spectroscopic method of claim 1, further comprising:
containing a sample in a container through which the electromagnetic radiation passes or from which the electromagnetic radiation emanates prior to reception by the optical detector.

13. The spectroscopic method of claim 12, wherein the container is upstream of the optical filter module.

14. The spectroscopic method of claim 12, wherein the container is downstream of the optical filter module.

15. The spectroscopic method of claim 1, wherein the optical detector, in conjunction with the optical filter module, generates one or more electrical signals indicative of electromagnetic radiation intensity over a sweep of wavelengths within each of the multiple wavelength bands.

16. The spectroscopic method of claim 1, comprising:
providing the electromagnetic radiation source.

17. The spectroscopic method of claim 16, wherein the electromagnetic radiation source is a producer of at least one member selected from the group consisting of visible light, infrared light, and ultraviolet light.

* * * * *